US011786751B2

United States Patent
Genier et al.

(10) Patent No.: US 11,786,751 B2
(45) Date of Patent: Oct. 17, 2023

(54) THERAPEUTIC ILLUMINATION ASSEMBLIES AND METHODS OF ILLUMINATING MEDICAL DEVICES AND BIOLOGICAL MATERIAL USING THE SAME

(71) Applicant: CORNING INCORPORATED, Corning, NY (US)

(72) Inventors: Michael Lucien Genier, Horseheads, NY (US); William Spencer Klubben, III, Boston, MA (US)

(73) Assignee: Corning Incorporated, Corning, NY (US)

( * ) Notice: Subject to any disclaimer, the term of this patent is extended or adjusted under 35 U.S.C. 154(b) by 127 days.

(21) Appl. No.: 16/720,841

(22) Filed: Dec. 19, 2019

(65) Prior Publication Data

US 2020/0121947 A1 Apr. 23, 2020

Related U.S. Application Data

(63) Continuation of application No. 15/185,328, filed on Jun. 17, 2016, now Pat. No. 10,549,114.
(Continued)

(51) Int. Cl.
*A61N 5/06* (2006.01)
*A61N 5/067* (2006.01)

(52) U.S. Cl.
CPC ............ *A61N 5/0624* (2013.01); *A61N 5/067* (2021.08); *A61N 2005/0602* (2013.01);
(Continued)

(58) Field of Classification Search
CPC .................. A61N 5/0624; A61N 5/067; A61N 2005/0654; A61N 2005/0651
See application file for complete search history.

(56) References Cited

U.S. PATENT DOCUMENTS 5,807,341 A * 9/1998 Heim .................... A61M 25/02
604/174
5,833,682 A 11/1998 Amplatz et al.
(Continued)

FOREIGN PATENT DOCUMENTS

CN 104010710 A 8/2014
EP 2854944 A1 4/2015
(Continued)

OTHER PUBLICATIONS

R. Paschotta, article on 'refraction' in the RP Photonics Encyclopedia, https://www.rp-photonics.com/refraction.html, accessed on May 16, 2022.*
(Continued)

*Primary Examiner* — Lynsey C Eiseman
*Assistant Examiner* — James Moss
(74) *Attorney, Agent, or Firm* — Svetlana Z. Short

(57) ABSTRACT

A therapeutic illumination assembly includes a catheter and a point source treatment fiber. The catheter comprises a catheter wall encircling a luminal fluid pathway. The point source treatment fiber is positioned within the luminal fluid pathway of the catheter. Further, the point source treatment fiber comprises a plurality of light emitting point sources intermittently positioned along a treatment length of the point source treatment fiber such that the plurality of light emitting point sources irradiate the catheter when the plurality of light emitting point sources emit light.

19 Claims, 16 Drawing Sheets

Related U.S. Application Data

(60) Provisional application No. 62/290,698, filed on Feb. 3, 2016.

(52) U.S. Cl.
CPC ...... *A61N 2005/063* (2013.01); *A61N 2005/0651* (2013.01); *A61N 2005/0654* (2013.01)

(56) References Cited

U.S. PATENT DOCUMENTS

| | | | |
|---|---|---|---|
| 5,989,245 A * | 11/1999 | Prescott | A61N 5/0616 606/14 |
| 6,551,346 B2 | 4/2003 | Crossley | |
| 8,404,273 B2 | 3/2013 | Baumgart et al. | |
| 8,585,681 B2 | 11/2013 | Boenig et al. | |
| 8,779,386 B2 | 7/2014 | Bak | |
| 8,980,174 B2 | 3/2015 | Haytman et al. | |
| 9,039,966 B2 | 5/2015 | Anderson et al. | |
| 9,067,059 B2 | 6/2015 | Bissig et al. | |
| 9,259,513 B2 | 2/2016 | Bedwell et al. | |
| 9,393,339 B2 | 7/2016 | Park et al. | |
| 9,439,989 B2 | 9/2016 | Lalicki et al. | |
| 9,550,005 B2 | 1/2017 | Lin et al. | |
| 9,795,466 B2 | 10/2017 | Piergallini et al. | |
| 9,808,647 B2 | 11/2017 | Rhodes et al. | |
| 9,925,390 B2 | 3/2018 | Yehezkel | |
| 9,943,379 B2 | 4/2018 | Gregg, II et al. | |
| 10,046,070 B1 | 8/2018 | Zaborsky et al. | |
| 10,166,402 B2 | 1/2019 | Brennan et al. | |
| 10,183,144 B2 | 1/2019 | Tang et al. | |
| 10,241,035 B2 | 3/2019 | Bonnick et al. | |
| 2001/0047195 A1 * | 11/2001 | Crossley | A61N 5/0601 607/88 |
| 2002/0019610 A1 * | 2/2002 | Bousquet | A61M 39/0247 604/175 |
| 2003/0233073 A1 * | 12/2003 | Purow | A61M 27/00 604/174 |
| 2006/0085052 A1 | 4/2006 | Feuerstein et al. | |
| 2009/0257910 A1 | 10/2009 | Segal | |
| 2009/0318816 A1 | 12/2009 | Knighton et al. | |
| 2010/0268151 A1 | 10/2010 | Mauge et al. | |
| 2011/0160681 A1 | 6/2011 | Dacey, Jr. et al. | |
| 2013/0035629 A1 | 2/2013 | Soltz et al. | |
| 2013/0267888 A1 | 10/2013 | Rhodes et al. | |
| 2014/0343478 A1 * | 11/2014 | Brennan | A61N 5/0624 604/20 |
| 2015/0080709 A1 | 3/2015 | Chaturvedi | |
| 2016/0151639 A1 * | 6/2016 | Scharf | A61N 5/0601 607/92 |
| 2018/0036443 A1 | 2/2018 | Messerly | |
| 2018/0056086 A1 | 3/2018 | Harari | |
| 2018/0147417 A1 | 5/2018 | Rantala | |
| 2018/0178031 A1 | 6/2018 | Wu | |
| 2018/0207302 A1 | 7/2018 | Vasilenko | |
| 2018/0304094 A1 | 10/2018 | Hicks et al. | |
| 2018/0326104 A1 | 11/2018 | Hawkins et al. | |

FOREIGN PATENT DOCUMENTS

| | | |
|---|---|---|
| JP | 05546575 B2 | 7/2014 |
| KR | 1362704 B1 | 2/2014 |
| KR | 1851576 B1 | 4/2018 |
| KR | 2018049757 A | 5/2018 |
| KR | 1892996 B1 | 8/2018 |
| KR | 2018135256 A | 12/2018 |
| KR | 2018135257 A | 12/2018 |
| SG | 11201603590 Y | 12/2014 |
| SG | 11201407227 B | 10/2017 |
| WO | 2013/177674 A1 | 12/2013 |
| WO | 2015168129 A1 | 11/2015 |
| WO | 2018009864 A1 | 1/2018 |
| WO | 2019/027478 A1 | 2/2019 |
| WO | 2019025808 A1 | 2/2019 |

OTHER PUBLICATIONS

"Catheter." Merriam-Webster.com Dictionary, Merriam-Webster, https://www.merriam-webster.com/dictionary/catheter. Accessed May 16, 2022.*

"Refraction." Merriam-Webster.com Dictionary, Merriam-Webster, https://www.merriam-webster.com/dictionary/refraction. Accessed May 17, 2022.*

R. Paschotta, RP Photonics Encyclopedia, https://www.rp-photonics.com/encyclopedia.html, accessed on Nov. 19, 2022.*

Bauco et al.; Medical Device Disinfecting System; U.S. Appl. No. 62/208,239, filed Aug. 21, 2015; pp. 1-39.

* cited by examiner

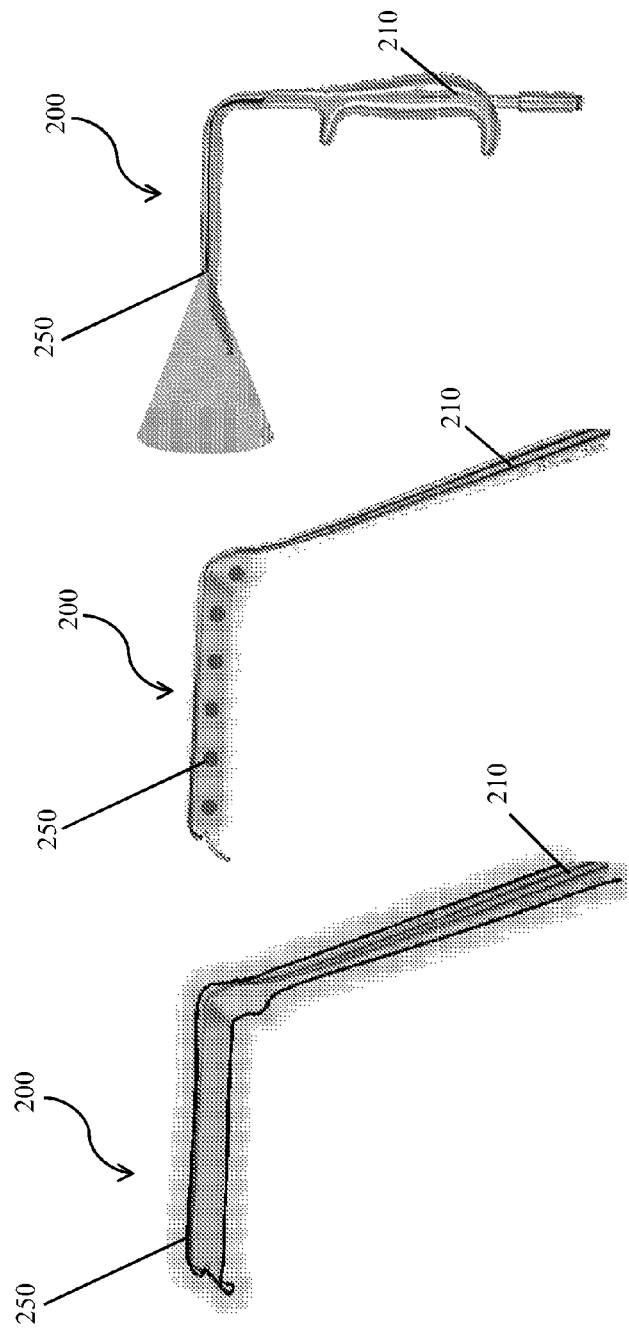

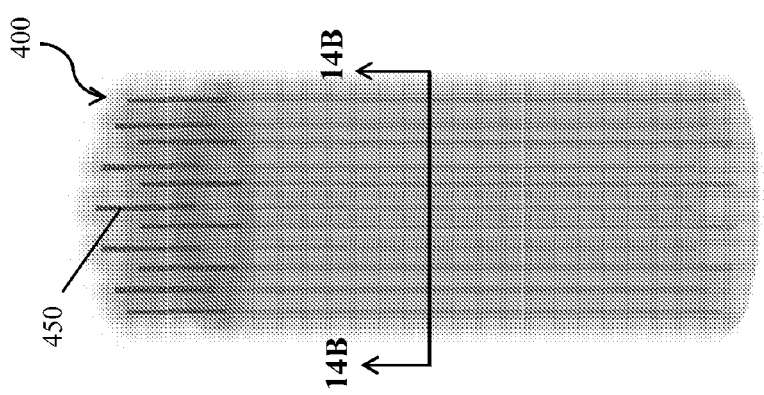
FIG. 14A
FIG. 14B
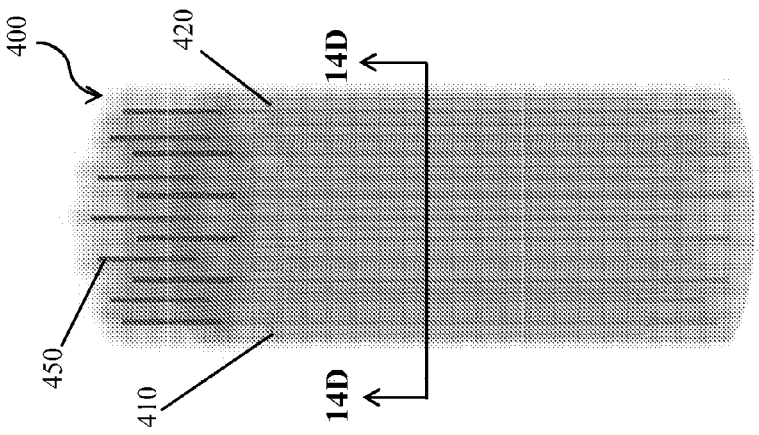
FIG. 14C
FIG. 14D
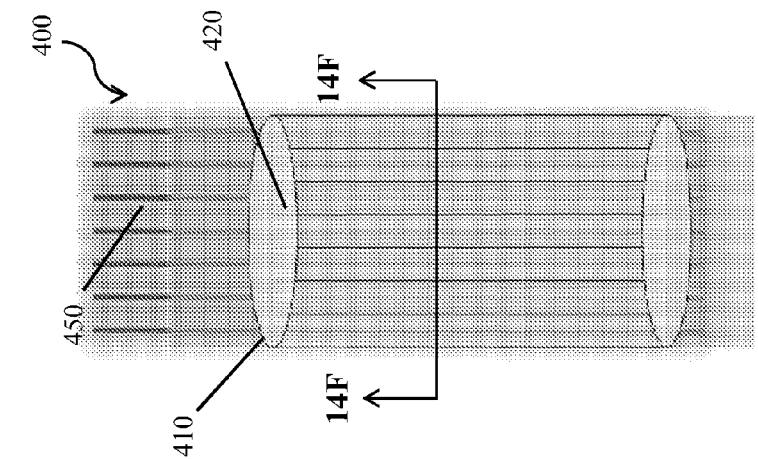
FIG. 14E
FIG. 14F
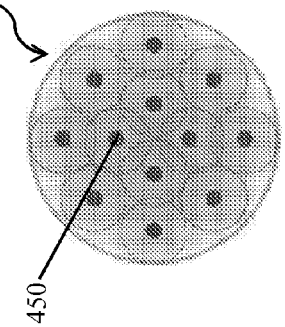
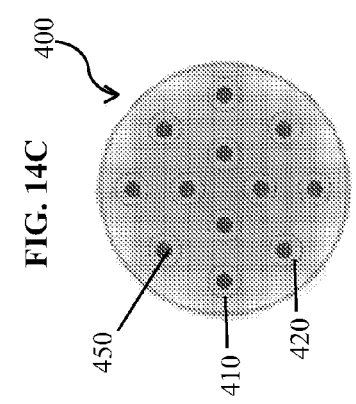
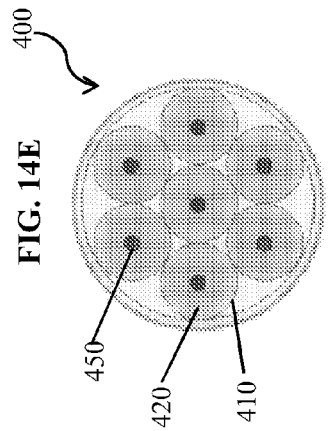

THERAPEUTIC ILLUMINATION ASSEMBLIES AND METHODS OF ILLUMINATING MEDICAL DEVICES AND BIOLOGICAL MATERIAL USING THE SAME

This application is a continuation of U.S. patent application Ser. No. 15/185,328 filed on Jun. 17, 2016, which claims the benefit of priority under 35 U.S.C. § 119 of U.S. Provisional Application Ser. No. 62/290,698, filed on Feb. 3, 2016, the content of which is relied upon and incorporated herein by reference in its entirety.

BACKGROUND

The present disclosure relates to therapeutic illumination assemblies. More specifically, the present disclosure introduces technology for therapeutic illumination assemblies having one or more light emitting point sources.

BRIEF SUMMARY

According to the subject matter of the present disclosure, a therapeutic illumination assembly includes a catheter and a point source treatment fiber. The catheter includes a catheter wall encircling a luminal fluid pathway. The point source treatment fiber is positioned within the luminal fluid pathway of the catheter. Further, the point source treatment fiber includes a plurality of light emitting point sources intermittently positioned along a treatment length of the point source treatment fiber such that the plurality of light emitting point sources irradiate the catheter when the plurality of light emitting point sources emit light.

In accordance with one embodiment of the present disclosure, a method of irradiating a catheter includes inserting an internal length of a catheter into a patient. The catheter includes a catheter wall encircling a luminal fluid pathway. The catheter includes an external length fluidly coupled to the internal length at an insertion region of the catheter. The method further includes inserting a point source treatment fiber includes a plurality of light emitting point sources intermittently positioned along a treatment length of the point source treatment fiber into the luminal fluid pathway of the catheter and irradiating the catheter using the plurality of light emitting point sources.

Although the concepts of the present disclosure are described herein with primary reference to some specific therapeutic illumination assembly configurations, it is contemplated that the concepts will enjoy applicability to therapeutic illumination assemblies having any configuration.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which:

FIG. 6A is a schematic illustration of a surgical device and a light diffusing optical fiber, according to one or more embodiments shown and described herein;

FIG. 6B is a schematic illustration of a surgical device and one or more light emitting point sources, according to one or more embodiments shown and described herein;

FIG. 6C is a schematic illustration of a surgical device and a single light emitting point source, according to one or more embodiments shown and described herein;

FIG. 14A is a schematic illustration of another therapeutic illumination assembly including one or more light emitting devices, according to one or more embodiments shown and described herein;

FIG. 14B is a cross-sectional illustration of the therapeutic illumination assembly of FIG. 14A, according to one or more embodiments shown and described herein;

FIG. 14C is a schematic illustration of another therapeutic illumination assembly including one or more light emitting devices and a fiber housing vessel, according to one or more embodiments shown and described herein;

FIG. 14D is a cross-sectional illustration of the therapeutic illumination assembly of FIG. 13C, according to one or more embodiments shown and described herein;

FIG. 14E is a schematic illustration of another therapeutic illumination assembly including one or more light emitting devices and a fiber housing vessel, according to one or more embodiments shown and described herein;

FIG. 14F is a cross-sectional illustration of the therapeutic illumination assembly of FIG. 14E, according to one or more embodiments shown and described herein;

DETAILED DESCRIPTION

Figure 1:
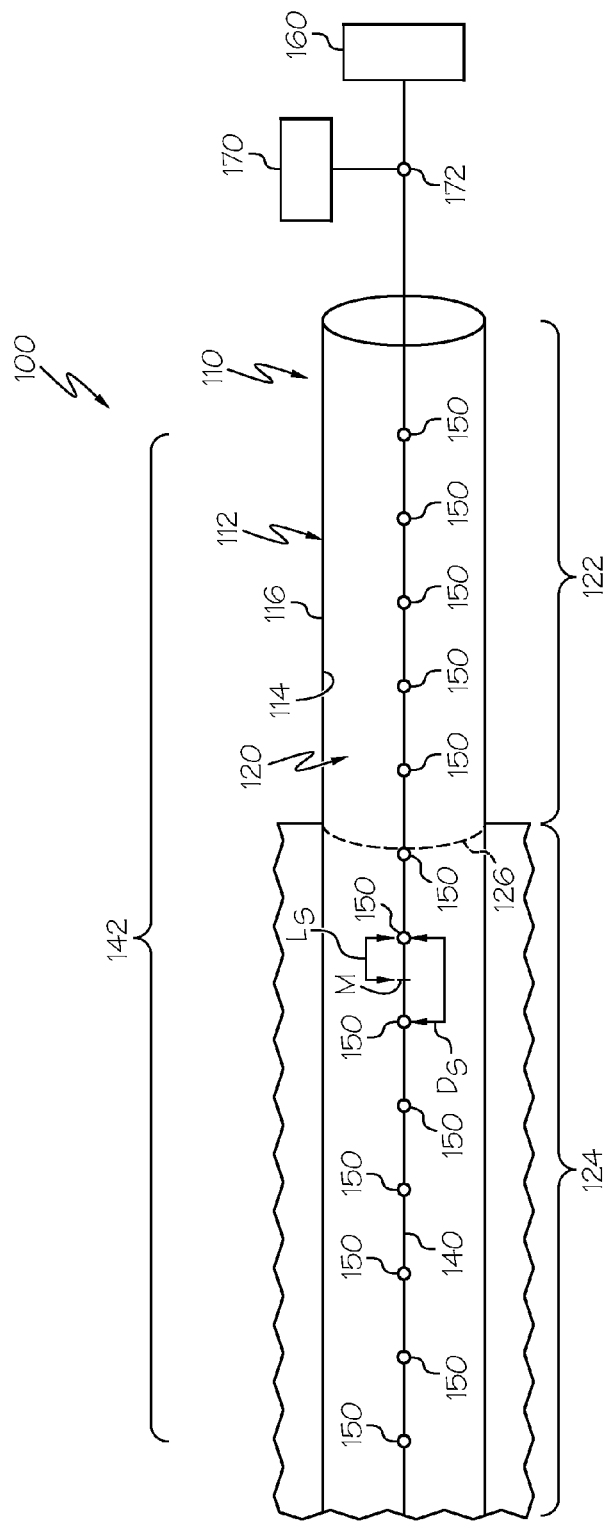
FIG. 1 is a schematic illustration of a therapeutic illumination assembly having a catheter and a point source treatment fiber, according to one or more embodiments shown and described herein.

FIG. 1 is a schematic illustration of a therapeutic illumination assembly 100. The therapeutic illumination assembly 100 comprises a catheter 110 and a point source treatment fiber 140. The catheter 110 comprises a catheter wall 112 encircling a luminal fluid pathway 120. The catheter wall 112 comprises a fluid facing surface 114 that confines the luminal fluid pathway 120 and an outer facing surface 116 opposite the fluid facing surface 114. The luminal fluid pathway 120 is configured to provide a pathway for fluid flowing through the catheter 110, for example, treatment fluids, biological fluids, or the like. Further, the catheter 110 may comprise any catheter, for example, a percutaneous catheter, an indwelling catheter, a peripherally inserted central catheter, a permanent catheter (permacath), or the like.

The point source treatment fiber 140 is positioned within the luminal fluid pathway 120 of the catheter 110. At least a portion of the point source treatment fiber 140 may contact the fluid facing surface 114, for example, coupled to the fluid facing surface 114 of the catheter wall 112. Further, at least a portion of the point source treatment fiber 140 may be positioned within the luminal fluid pathway 120 without contacting the fluid facing surface 114 of the catheter wall 112. The point source treatment fiber 140 comprises a plurality of light emitting point sources 150 intermittently positioned along a treatment length 142 of the point source treatment fiber 140 such that the plurality of light emitting point sources 150 irradiate the catheter 110 when the plurality of light emitting point sources 150 emit light. The treatment length 142 comprises the length of the point source treatment fiber 140 along which the plurality of light emitting point sources 150 are positioned, for example, a total length of the point source treatment fiber 140 or a partial length of the point source treatment fiber 140.

The plurality of light emitting point sources 150 may comprise a plurality of diodes positioned along the treatment length 142 of the point source treatment fiber 140, for example, one or more laser diodes, one or more light emitting diodes (LED), or a combination thereof. The point source treatment fiber 140 may comprise a guide wire and the plurality of diodes may be intermittently positioned along the guide wire, for example, intermittently coupled to the guide wire. Further, the plurality of light emitting point sources 150 may comprise an end of a transmissive optical fiber, a filament, a gaseous based illumination device, such as an incandescent bulb, an arc lamp, or the like. Further, the one or more light emitting point sources 150 may emit light comprising a wavelength of between about 200 nm and about 2000 nm for example, 350 nm, 405 nm, 500 nm, 650 nm, 860 nm, 870 nm, 880 nm, or the like. The one or more light emitting point sources 150 may be configured to both generate and output light. Alternatively, the one or more light emitting point sources 150 may be optically coupled to a therapeutic light source 160 configured to generate light such that the one or more light emitting point sources 150 may output light when the therapeutic light source 160 generates light.

The point source treatment fiber 140 may comprise a therapeutic optical fiber optically coupled to the therapeutic light source 160 and the plurality of light emitting point sources 150 may comprise one or more fiber defect regions intermittently positioned along the treatment length 142 of the therapeutic optical fiber, one or more fiber gratings intermittently positioned along the treatment length 142 of the therapeutic optical fiber, or combinations thereof. Further, the therapeutic optical fiber may comprise a light diffusing optical fiber intermittently coated with an opaque coating such that uncoated portions of the light diffusing optical fiber comprise the plurality of light emitting point sources 150.

Still referring to FIG. 1, the plurality of light emitting point sources 150 may be equally spaced along the treatment length 142 of the point source treatment fiber 140. Further, the plurality of light emitting point sources 150 may be spaced such that when the plurality of light emitting point sources 150 emit light, locations along the catheter wall 112 aligned with a midpoint M between each individual light emitting point source 150 receive an amount of irradiation between about 50% and about 95% of the amount of irradiation received by locations along the catheter wall 112 aligned with each individual light emitting point sources 150 of the plurality of light emitting point sources 150, for example, about 55%, 60%, 65%, 70%, 75%, 80%, 85%, 90%, or the like. Further, the plurality of light emitting point sources 150 may comprise any spacing relationship along the treatment length 142 of the point source treatment fiber 140.

As depicted in FIG. 1, the point source treatment fiber 140 may be coupled to a motion actuator 170 at an actuator coupling location 172 of the point source treatment fiber 140. In operation, the motion actuator 170 may translate the point source treatment fiber 140 within the luminal fluid pathway 120 of the catheter 110, for example, linearly, radially, circumferentially, or the like. The motion actuator 170 may comprise any actuating device, for example, an electric actuator (e.g., an electric motor), a mechanical actuator, a hydraulic actuator, a pneumatic actuator, or the like. Moreover, the plurality of light emitting point sources 150 may operate as a boundary condition by stopping bacteria from traversing down the catheter 110, for example, by removing the bacteria.

Referring still to FIG. 1, a method of irradiating the catheter 110 is contemplated. The method may comprise inserting an internal length 124 of the catheter 110 into a patient at an insertion location of the patient. The catheter 110 may further comprise an external length 122 fluidly coupled to the internal length 124 at an insertion region 126 of the catheter 110. When the internal length 124 of the catheter 110 is inserted into the patient, the internal length 124 is positioned in the patient, the insertion region 126 is substantially co-located with the insertion location of the patient, and the external length 122 is positioned outside the patient.

Next, the method may comprise inserting the point source treatment fiber 140 comprising the plurality of light emitting point sources 150 intermittently positioned along the treatment length 142 of the point source treatment fiber 140 into the luminal fluid pathway 120 of the catheter 110. The point source treatment fiber 140 may comprise any of the point source treatment fibers 140 described above. The point source treatment fiber 140 may extend within the luminal fluid pathway 120 of the catheter 110 along at least a portion of the external length 122 of the catheter 110 and/or at least a portion of the internal length 124 of the catheter 110. Further, the point source treatment fiber 140 may extend within the luminal fluid pathway 120 along at least a portion both the internal length 124 and the external length 122 such that at least a portion of the point source treatment fiber 140 is positioned at the insertion region 126 of the catheter 110. Moreover, at least a portion of the point source treatment fiber 140 may be coupled to the fluid facing surface 114 of the catheter wall 112, for example, at the insertion region 126 of the catheter 110. Next, the method comprises irradiating the catheter 110 using the plurality of light emitting point sources 150. By irradiating the catheter 110, the light emitting point sources 150 may irradiate the tissue surrounding the internal length 124 of the catheter 110 and irradiate fluid traversing the luminal fluid pathway 120, and/or a percutaneous lesion near the catheter 110, for example, to disinfect the catheter 110, fluid traversing the catheter 110, and/or tissue surrounding the catheter 110.

The method may further comprise actuating the motion actuator 170 to linearly, radially, and/or circumferentially translate the point source treatment fiber 140. For example, the motion actuator 170 may linearly reciprocate the point source treatment fiber 140 along a stroke length Ls of the point source treatment fiber 140. For example, the stroke length Ls may be equal to one-half a spacing distance Ds between adjacent light emitting point sources 150. Alternatively or additionally, the method may further comprise actuating the motion actuator 170 to radially reciprocate the point source treatment fiber 140 with respect to the catheter wall 112 of the catheter 110, for example, radially reciprocate the point source treatment fiber 140 between a cross-sectional center point of the catheter 110 and one or more locations along the catheter wall 112 or between the cross sectional center point and the catheter wall 112. Alternatively or additionally, the method may further comprise actuating the motion actuator 170 to translate the point source treatment fiber 140 circumferentially along to the catheter wall 112 of the catheter 110.

Figure 2:
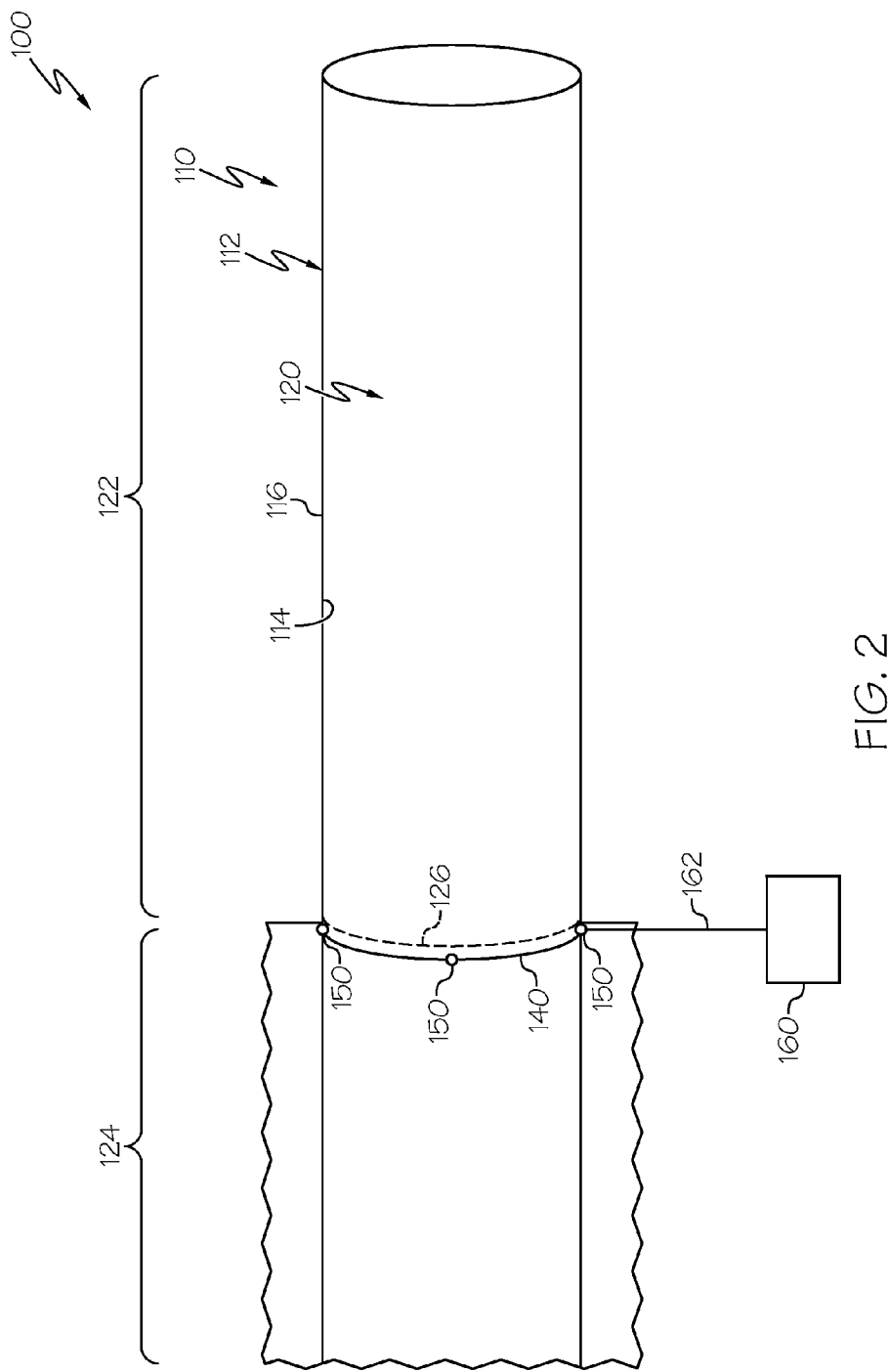
FIG. 2 is a schematic illustration of a therapeutic illumination assembly having a catheter and one or more light emitting point sources, according to one or more embodiments shown and described herein.

Referring now to FIG. 2, the therapeutic illumination assembly 100 is depicted comprising the catheter 110 and one or more light emitting point sources 150. The one or more light emitting point sources 150 may be intermittently positioned on the outer facing surface 116, for example, coupled to the outer facing surface 116 of the catheter wall 112. The one or more light emitting point sources 150 may comprise a plurality of diodes coupled to the outer facing surface 116 of the catheter wall 112, for example, one or more laser diodes, one or more light emitting diodes (LED), or a combination thereof. The one or more light emitting point sources 150 may be intermittently positioned along a treatment length 142 of a point source treatment fiber 140, which may comprise a guide wire, a therapeutic optical fiber optically coupled to a therapeutic light source 160, or the like. Further, the point source treatment fiber 140 may be optically coupled to the therapeutic light source 160 using a transmission fiber 162. Moreover, the one or more light emitting point sources 150 may comprise any of the light emitting point sources 150 described above.

As depicted in FIG. 2, at least a portion of the treatment length 142 of the point source treatment fiber 140 may be coupled to the outer facing surface 116 of the catheter 110 at the insertion region 126 of the catheter 110 and least a portion of the treatment length 142 of point source treatment fiber 140 may encircle the catheter wall 112 of the catheter 110 at the insertion region 126 of the catheter 110. Further, when the internal length 124 of the catheter 110 is positioned within the patient, the one or more light emitting point sources 150 may be positioned on the outer facing surface 116 of the catheter wall 112 at the insertion region 126 of the catheter 110 such that the plurality of light emitting point sources 150 irradiate the insertion region 126 of the catheter 110 when the plurality of light emitting point sources 150 emit light. Further, the plurality of light emitting point sources 150 intermittently positioned on the outer facing surface 116 may be used to irradiate a percutaneous lesion near the catheter 110.

Figure 3:
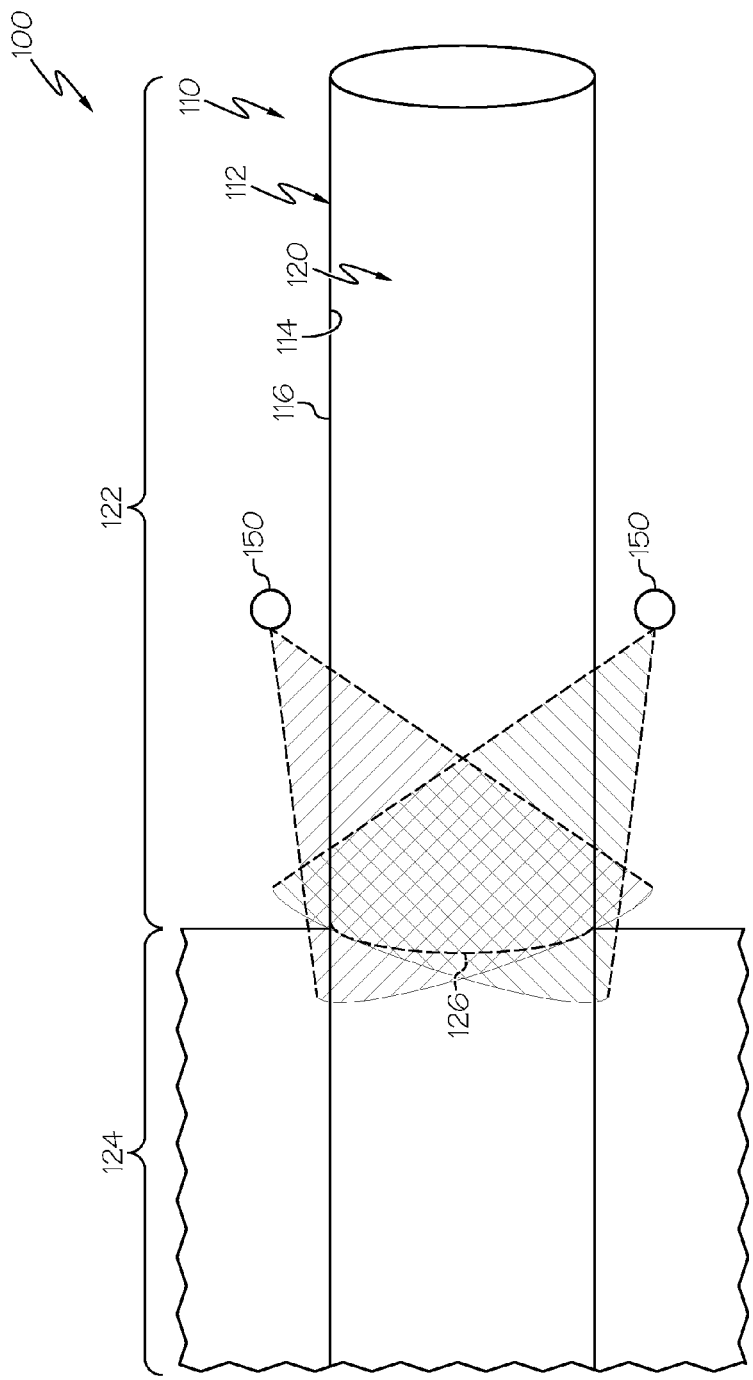
FIG. 3 is a schematic illustration of another therapeutic illumination assembly having a catheter and one or more light emitting point sources, according to one or more embodiments shown and described herein.

Referring now to FIG. 3, the therapeutic illumination assembly 100 is depicted comprising the catheter 110 and one or more light emitting point sources 150 positioned at a location spaced apart from the catheter 110, external to the catheter 110, for example, positioned at a location spaced apart from the outer facing surface 116 of the catheter wall 112. In operation, the one or more light emitting point sources 150 may be positioned and oriented such that when the one or more light emitting point sources 150 emit light, the emitted light may illuminate the insertion region 126 of the catheter 110 when the internal length 124 of the catheter 110 is positioned within the patient. The one or more light emitting point sources 150 may comprise any of the light emitting point sources 150 described above. Further, the one or more light emitting point sources 150 may comprise an end of a transmission optical fiber.

Figure 4:
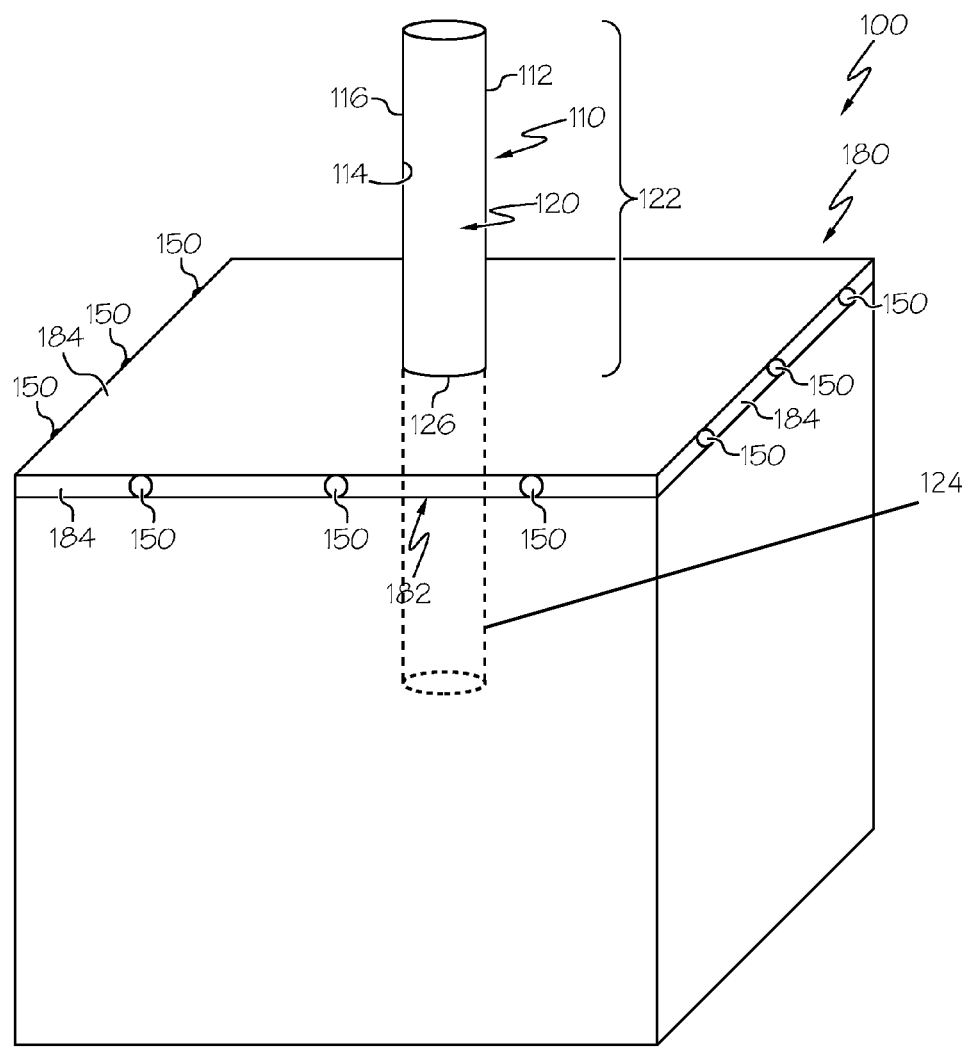
FIG. 4 is a schematic illustration of a therapeutic illumination assembly having a therapeutic light patch and one or more light emitting point sources, according to one or more embodiments shown and described herein.
Figure 5:
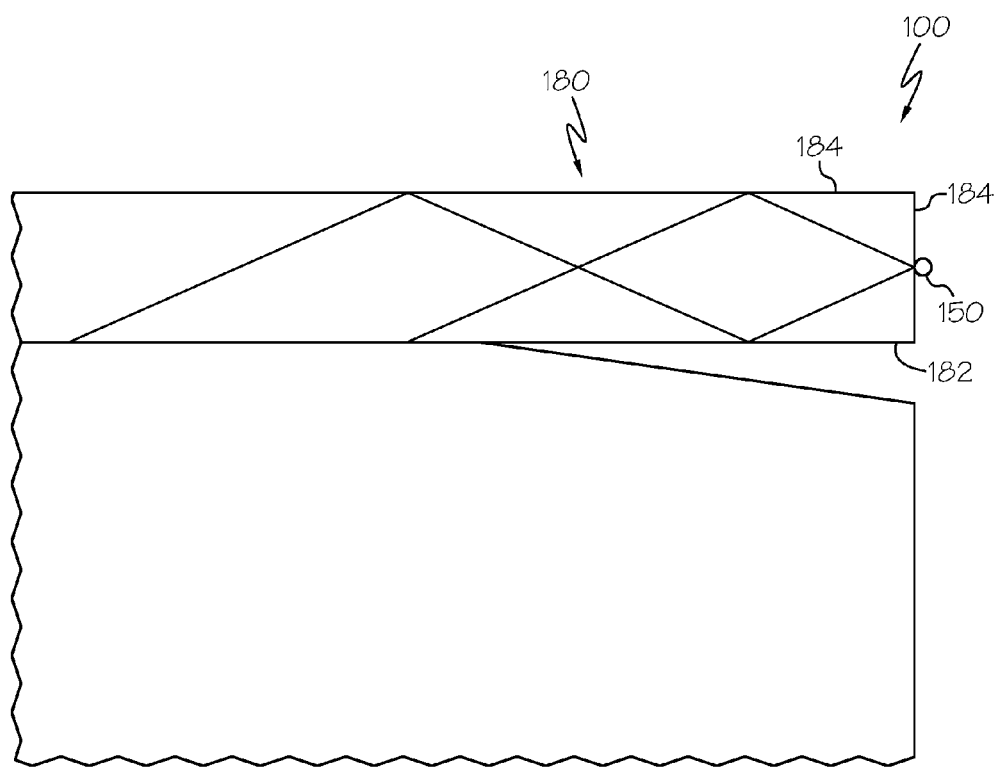
FIG. 5 is a schematic illustration of another therapeutic illumination assembly having a therapeutic light patch and one or more light emitting point sources, according to one or more embodiments shown and described herein.

Referring now to FIGS. 4-5, the therapeutic illumination assembly 100 may comprise a therapeutic illumination patch 180 and one or more light emitting point sources 150. The therapeutic illumination patch 180 may comprise a wound facing surface 182 and one or more outer facing surfaces 184 and may comprise an optically transmissive material. Further, the one or more light emitting point sources 150 are each optically coupled to the therapeutic illumination patch 180 such that the plurality of light emitting point sources 150 irradiate the therapeutic illumination patch 180 when the plurality of light emitting point sources 150 output light. For example, the plurality of light emitting point sources 150 may be affixed to one or more of the outer facing surfaces 184 of the therapeutic illumination patch 180. Moreover, the therapeutic illumination patch 180 may comprise an adhesive material disposed on the wound facing surface 182. The adhesive material may comprises a pressure sensitive adhesive, an acrylic adhesive, or a combination thereof.

As depicted in FIG. 4, the optically transmissive material of the therapeutic illumination patch 180 may be optically diffusive such that when the plurality of light emitting point sources 150 irradiate the therapeutic illumination patch 180, at least a portion of light emitted from the plurality of light emitting point sources 150 traverses from the optically transmissive material of the therapeutic illumination patch 180 through the wound facing surface 182 of the therapeutic illumination patch 180. Further, when the wound facing surface 182 of the therapeutic illumination patch 180 is positioned adjacent to a patient, for example, coupled to the patient, light that traverses through the wound facing surface 182 may irradiate tissue and/or skin of the patient, for example, a wound of the patient.

As depicted in FIG. 5, the therapeutic illumination patch 180 may comprise a waveguide structurally and compositionally configured such that at least a portion of the light emitted from the plurality of light emitting point sources 150 is subject to internal reflection at the wound facing surface 182 of the therapeutic illumination patch 180 and is subject to at least partial refraction at an optical interface formed by a patient surface and at least a portion of the wound facing surface 182 of the therapeutic illumination patch 180. In operation, when the wound facing surface 182 of the therapeutic illumination patch 180 is in contact with a patient, for example, positioned on tissue and/or skin of the patient, such as a wound of the patient, light traversing the therapeutic illumination patch may subject to at least partial refraction at the optical interface formed by contact with the patient such that at least a portion of light traversing the therapeutic illumination patch 180 irradiates the tissue and/or the skin of the patient, for example, a wound of the patient.

Figures 7A, 7B:
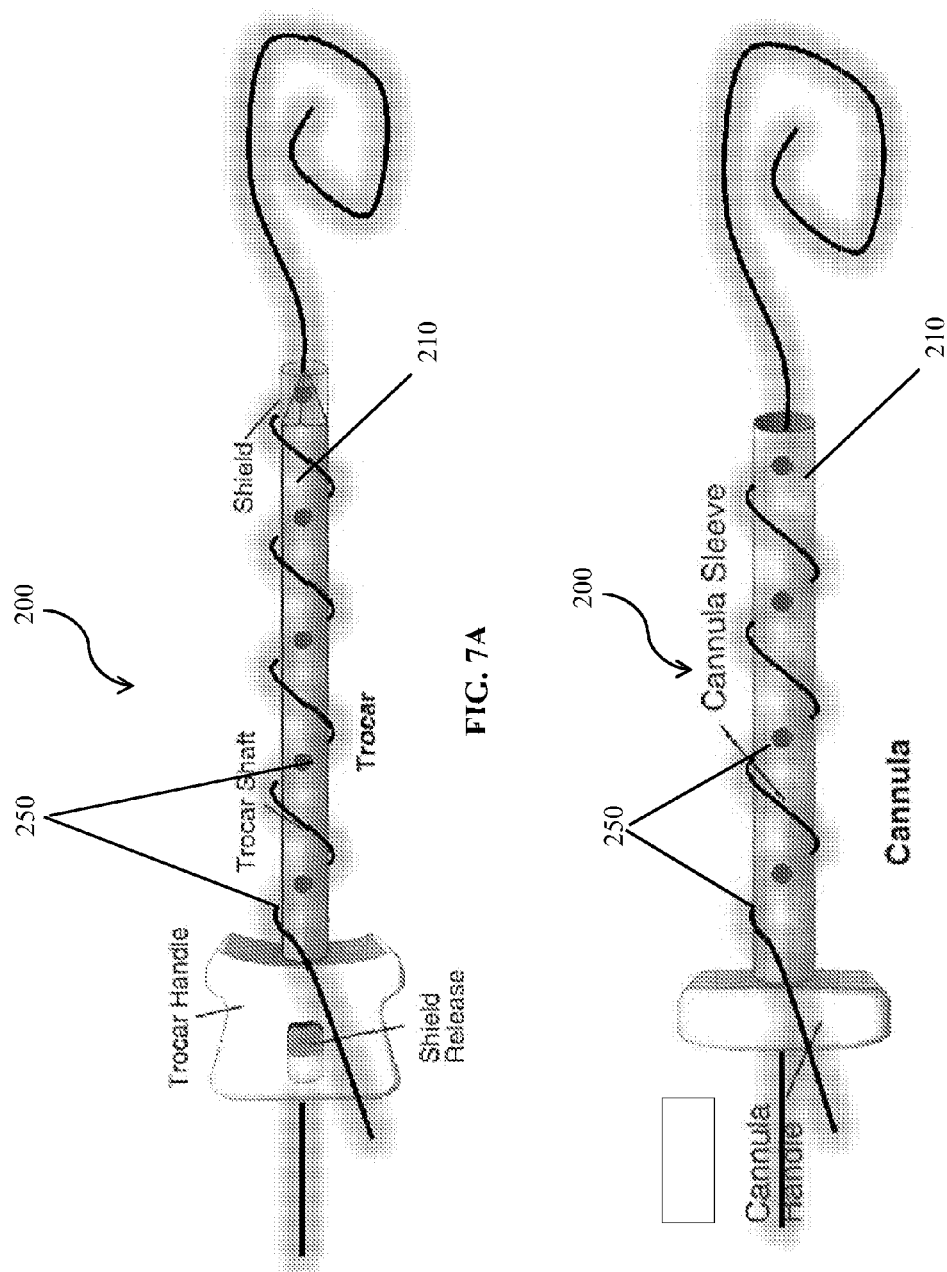
FIG. 7A is a schematic illustration of a trocar and one or more light emitting devices, according to one or more embodiments shown and described herein.
FIG. 7B is a schematic illustration of a cannula and one or more light emitting devices, according to one or more embodiments shown and described herein.

As depicted in FIGS. 6A-6C and 7A-7B, example therapeutic assemblies 200 may comprise one or more light emitting devices 250 optically and/or physically coupled to one or more surgical devices 210. As depicted in FIG. 6A, the one or more light emitting devices 250 comprise one or more light diffusing optical fibers coupled to a surgical device 210, for example, a surgical retractor. As depicted in FIGS. 6B and 6C, the one or more light emitting devices 250 may comprise one or more light emitting point sources, for example, any of the light emitting point sources 150 described above with respect to FIGS. 1-5, and the surgical device 210 may comprise a surgical retractor. For example, FIG. 6B depicts a plurality of light emitting point sources positioned along a length of the surgical retractor, for example, along a blade of the surgical retractor. Further, FIG. 6C depicts a single light emitting point source positioned at a blade end of the surgical device such that the single light emitting point source is oriented to emit light in direction away from the blade end. As depicted in FIG. 7A, the one or more light emitting devices 250 may be coupled to a surgical device 210 comprising a trocar. As depicted in FIG. 7B, the one or more light emitting devices 250 may be coupled to a surgical device 210 comprising a cannula. As depicted in both FIGS. 7A and 7B, the one or more light emitting devices 250 may wrap around, extend through, or otherwise attach to the trocar and the cannula. Further, the one or more light emitting devices 250 of FIGS. 7A and 7B may comprise one or more light diffusing optical fibers and/or one or more light emitting point sources, for example, any of the light emitting point sources 150 described above with respect to FIGS. 1-5.

Figure 8B:
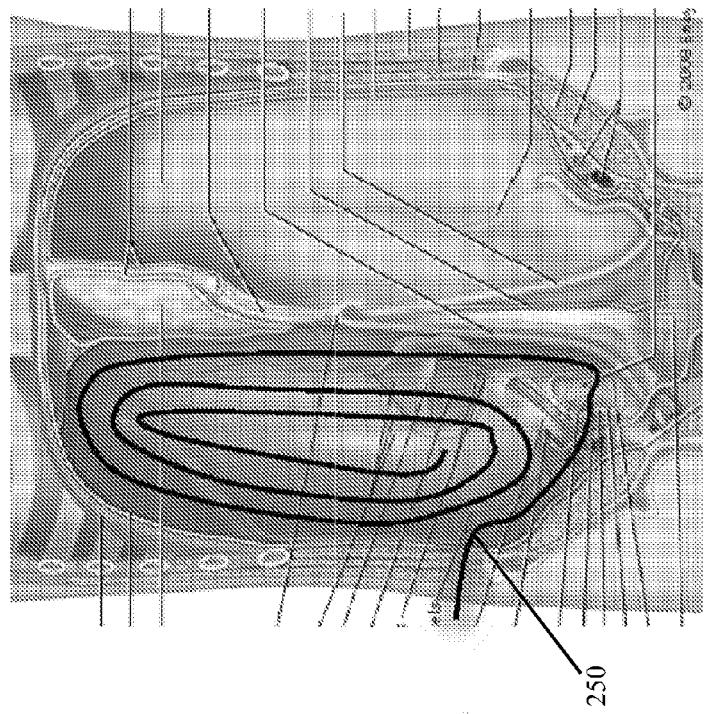
FIG. 8B is another schematic illustration of one or more light emitting devices positioned within one or more surgical cavities, according to one or more embodiments shown and described herein.
Figure 8A:
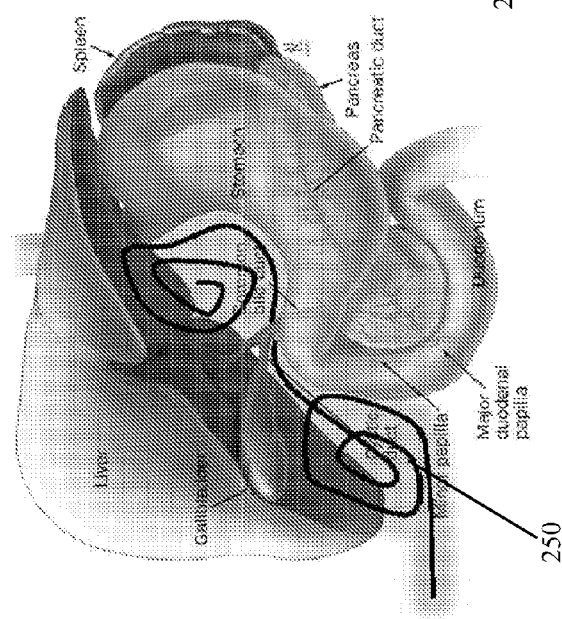
FIG. 8A is a schematic illustration of one or more light emitting devices positioned within one or more surgical cavities, according to one or more embodiments shown and described herein.
Figure 9:
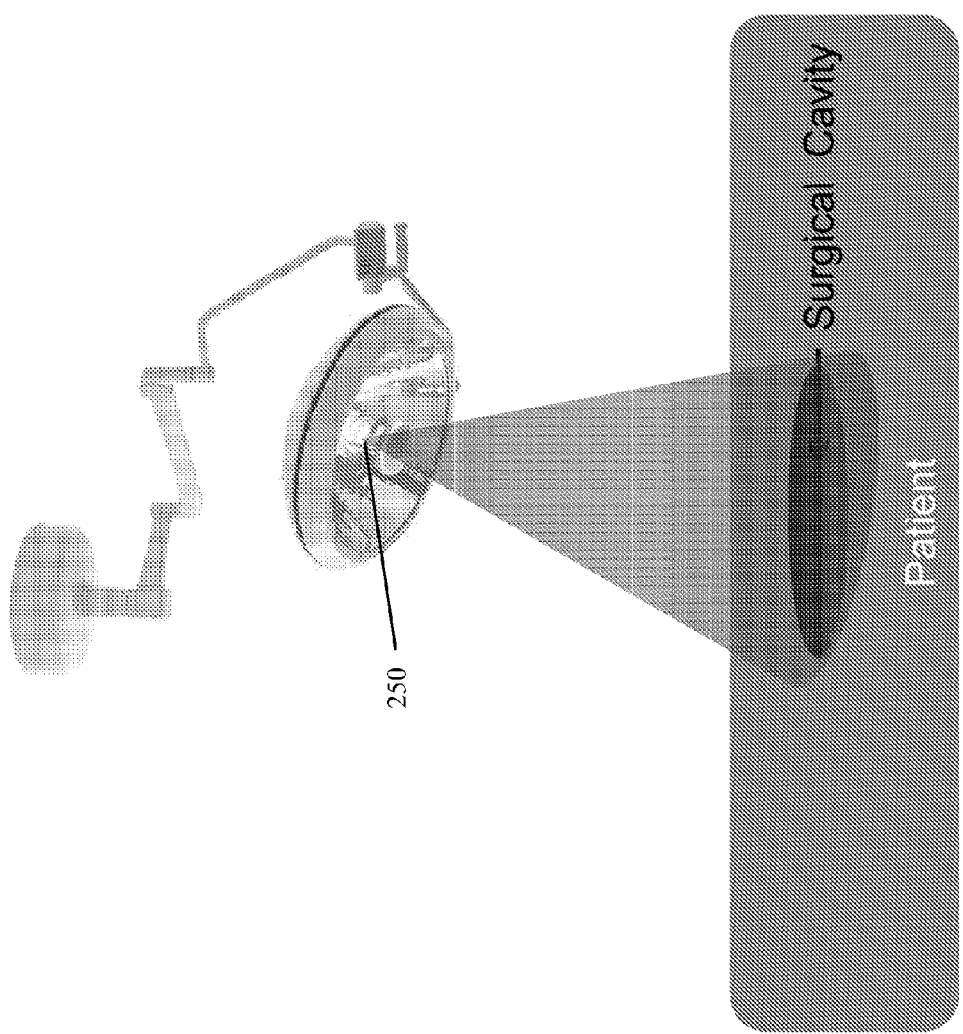
FIG. 9 is a schematic illustration of a movable surgical lamp, according to one or more embodiments shown and described herein.

Referring now to FIGS. 8A and 8B, the one or more light emitting devices 250 comprising light diffusing optical fiber and/or one or more light emitting point sources may be positioned within one or more surgical cavities of a patient, for example, positioned between a liver and a stomach, as depicted in FIG. 8A, positioned within the thoracic and abdominal cavities, as depicted in FIG. 8B, or positioned within any surgical cavity. In operation, the one or more light emitting devices 250 may emit light into the surgical cavity and irradiate tissue surrounding the surgical cavity, fluid located within the surgical cavity, and/or one or more surgical tools positioned within the surgical cavity, for example, at wavelengths that may disinfect each of the same, for example, wavelengths between 200 nm and 2000 nm, for example 405 nm. Referring now to FIG. 9, the one or more light emitting devices 250 may be positioned apart from a patient and a surgical cavity of a patient, for example, coupled to a movable surgical lamp such that the one or more light emitting devices 250 may emit light to irradiate and disinfect the surgical cavity and areas of the patients surrounding the surgical cavity.

Figure 10B:
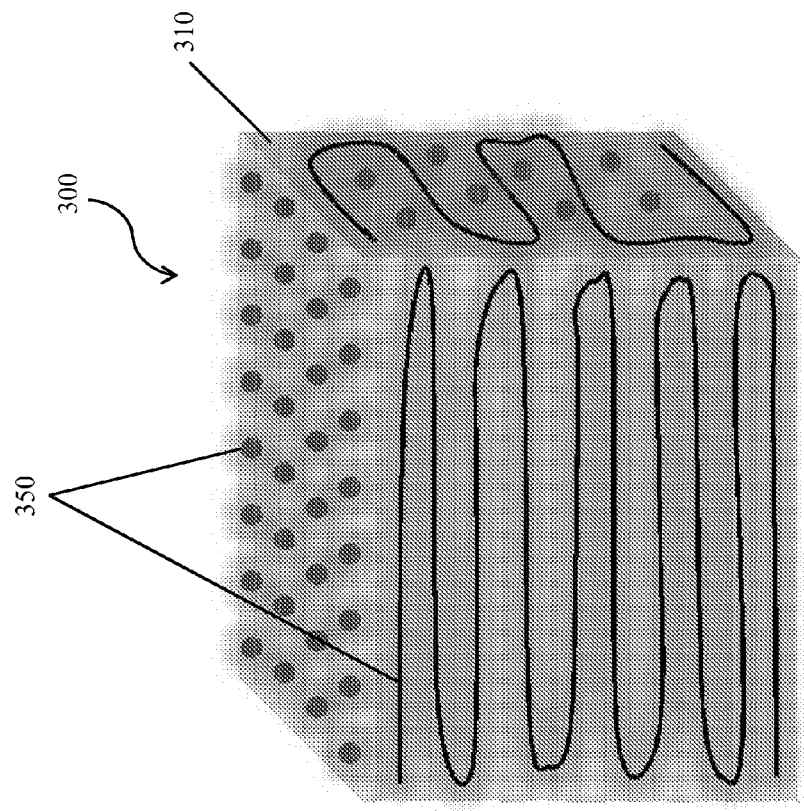
FIG. 10B is a schematic illustration of one or more light emitting devices coupled to another tissue housing device, according to one or more embodiments shown and described herein.
Figure 10A:
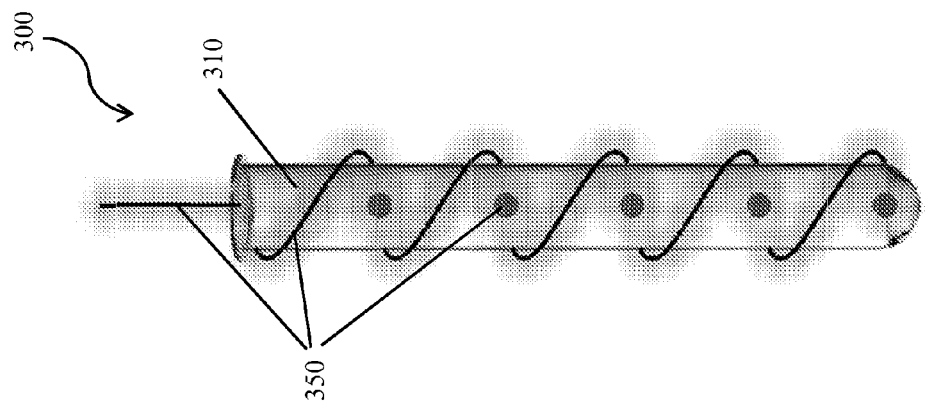
FIG. 10A is a schematic illustration of one or more light emitting devices coupled to a tissue housing device, according to one or more embodiments shown and described herein.
Figure 10C:
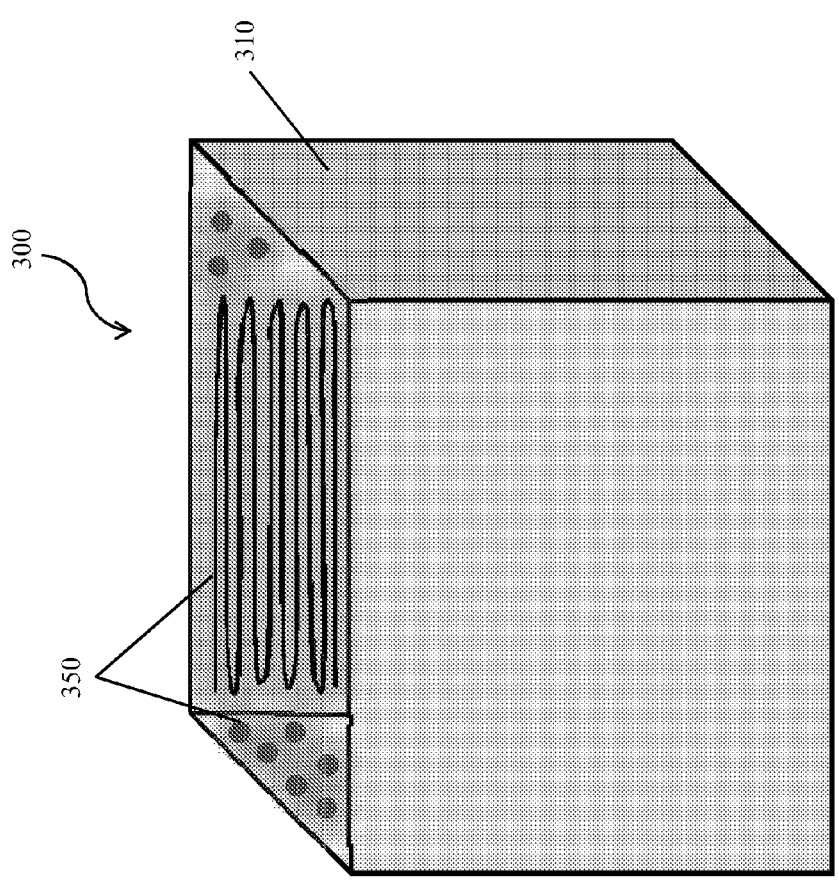
FIG. 10C is a schematic illustration of one or more light emitting devices coupled to a tissue transplant housing device, according to one or more embodiments shown and described herein.

Referring now to FIGS. 10A and 10B, example therapeutic illumination assemblies 300 are depicted that comprise one or more light emitting devices 350 optically and/or physically coupled to a tissue housing device 310 such that the one or more light emitting devices 350 may irradiate liquid and/or soft tissues housed within the tissue housing device 310. For example, the one or more light emitting devices 350 may be coupled to one or more interior surfaces of the tissue housing device 310 and/or one or more exterior surfaces of the tissue housing device 310, for example, when the tissue housing device 310 comprises an optically transmissive material. As depicted in FIG. 10C, the tissue housing device 310 may comprise a tissue transplant housing device for housing one or more organs, tissues, or the like, for transport between locations. Further, the one or more light emitting devices 350 may be coupled to an interior surface of the tissue transplant housing device to irradiate the one or more organs, tissues, or the like, housed within the tissue transplant housing device.

Figure 11:
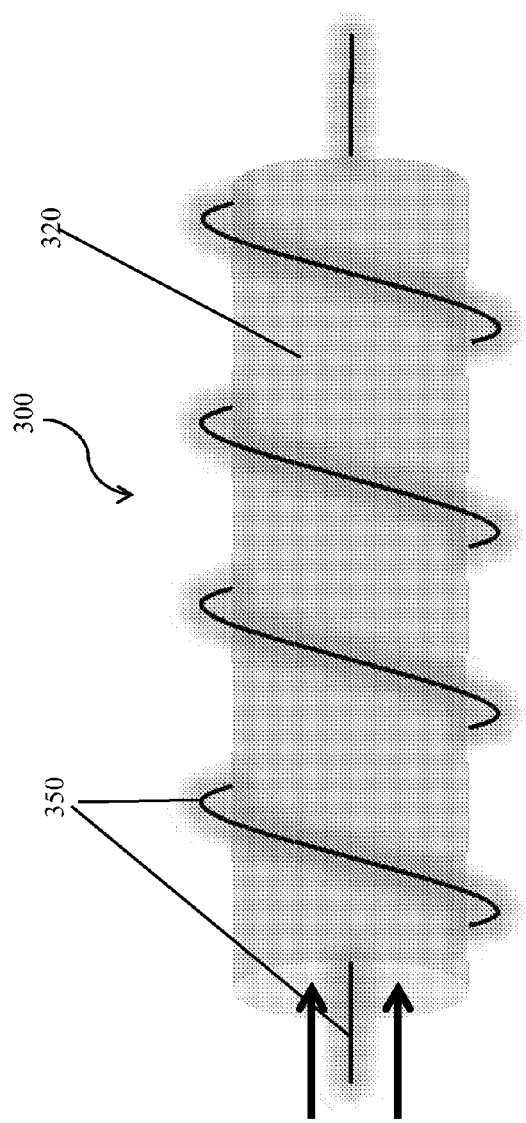
FIG. 11 is a schematic illustration of one or more light emitting devices coupled to a tissue disinfecting device, according to one or more embodiments shown and described herein.

Referring now to FIG. 11, an example therapeutic illumination assembly 300 is depicted comprising one or more light emitting devices 350 optically and/or physically coupled to a tissue disinfecting device 320 such that the one or more light emitting devices 350 may irradiate liquid, gases, and/or soft tissues traversing the tissue disinfecting device 320. In operation, soft tissues, biological fluids, treatment fluids, gases, or the like, may traverse the tissue disinfecting device 320 to disinfect these tissues and/or fluids. Further, the one or more light emitting devices 350 of FIGS. 10A-10C and 11 may comprise one or more light diffusing optical fibers and/or one or more light emitting point sources, for example, any of the light emitting point sources 150 described above with respect to FIGS. 1-5.

Figure 12:
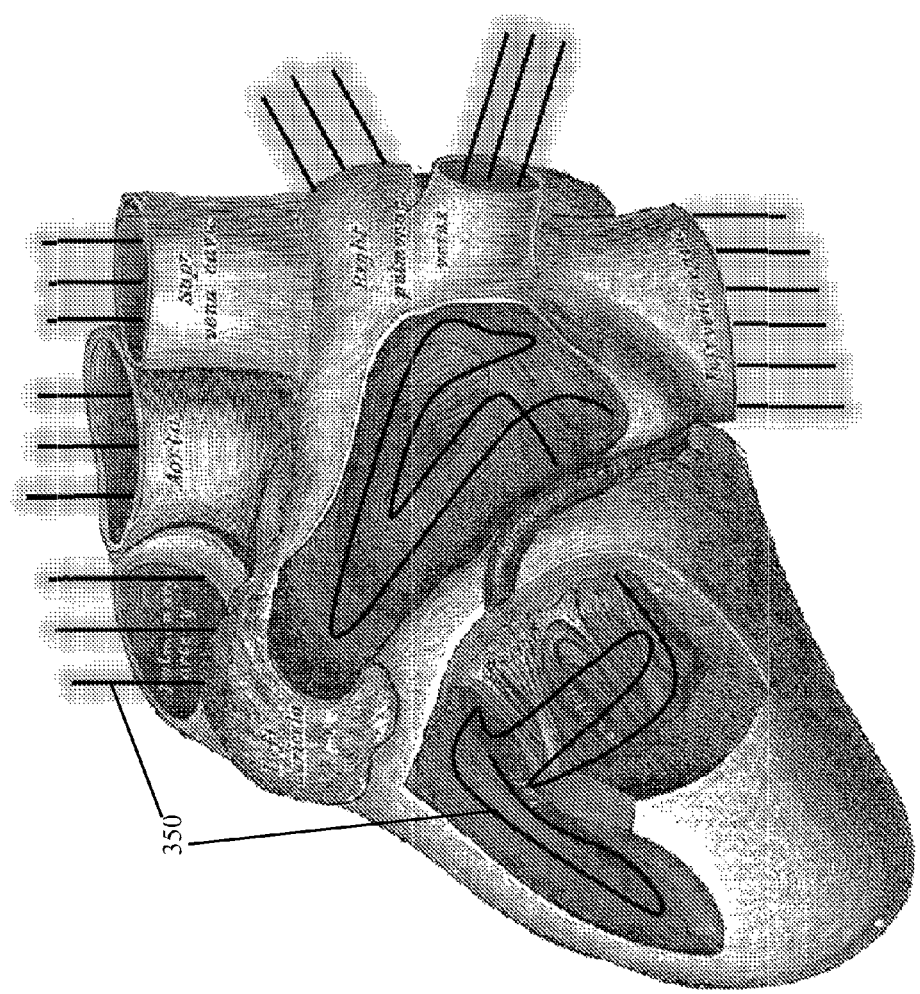
FIG. 12 is a schematic illustration of one or more light emitting devices positioned within and around one or more cavities and/or lumens of an organ or tissue, according to one or more embodiments shown and described herein.

Referring now to FIG. 12, the one or more light emitting devices 350 may be positioned within one or more cavities or lumens within an organ or tissue, for example, a heart or other organ. Further, the one or more light emitting devices 350 may be positioned around and/or on an organ or tissue, for example, wrapped around the organ or tissue. For example, the one or more light emitting devices 350 may be positioned within the luminal organ or tissue before and/or during transport of the luminal organ or tissue, for example, before a transplant procedure such that the one or more light emitting devices 350 may emit light to irradiate the cavities of the luminal organ or tissue, for example, to disinfect the luminal organ or tissue. Further, the one or more light emitting devices 350 may be positioned within an organ or tissue as depicted in FIG. 12 while the organ or tissue traverses the tissue disinfecting device 320 of FIG. 11.

Referring now to FIGS. 13A-15B, a method of irradiating, in situ, biological fluids flowing through luminal regions (e.g., blood vessels) using a therapeutic illumination assembly 400 is contemplated. The therapeutic illumination assembly 400 may comprise a fiber housing vessel 410 and one or more light emitting devices 450, which may each be positioned within luminal regions of a patient. The fiber housing vessel 410 comprises one or more housing vessel fluid pathways 420 and the one or more light emitting devices 450 may be positioned within the one or more housing vessel fluid pathways 420. Further, the housing vessel fluid pathways 420 may be cross-sectionally spaced such that the one or more light emitting devices 450 positioned within the housing vessel fluid pathways 420 are cross-sectionally spaced apart.

The one or more light emitting devices 450 may comprise one or more light diffusing optical fibers and/or one or more light emitting point sources, for example, any of the light emitting point sources 150 described above with respect to FIGS. 1-5, such as an optical fiber comprising glass, polymer, or other transparent material, a light emitting diode, a light emitting metallic element, or the like. When the one or more light emitting devices 450 comprise fibers such as light diffusing optical fibers, point source treatment fibers, therapeutic optical fibers, or the like, the fibers may extend within the housing vessel fluid pathways 420. Further, optical fibers, for example, light diffusing optical fibers, may be thin, flexible, and durable and thus are advantageous for insertion into a living and moving organism, for example, into the aorta of the inferior vena cava, and/or into an insertion region of a leg, neck, arm, or the like. Further, the one or more light emitting devices 450 may be optically coupled to at least one therapeutic light source configured to emit light.

In operation, biological fluid flowing through the one or more luminal regions of the patient may be irradiated using light output by the one or more light emitting devices 450, disinfecting the biological fluid without the bacteria becoming resistant to the irradiation treatment. Further, once light irradiates the biological fluid, the light may be absorbed and/or scattered by the biological fluid. In operation, the light emitting devices 450 may emit light at a wavelength between about 200 nm and about 2000 nm, for example, about 405 nm, to irradiate the biological fluid and irradiate any microorganisms present in the biological fluid. Any biological fluids are contemplated, for example, blood or whole blood, which may comprise of a variety of chemicals, biological markers, human cells, or the like. Further, the method of irradiating biological fluids flowing through one or more luminal regions may be may be used to treat sepsis in the patient.

As stated above, the one or more light emitting devices 450 may comprise light diffusing optical fibers, for example Corning™ Fibrance™ light diffusing optical fibers. In operation, light diffusing optical fiber may be advantageous because light diffusing optical fiber is configured to emit continual illumination, allowing the light diffusing optical fiber to continually disinfect of blood flowing through the luminal regions of the patient. Further, one or more light diffusing optical fibers, for example Corning™ Fibrance™ light diffusing optical fiber may comprise glass and may emit light at a high transmission rate.

Figure 13E:
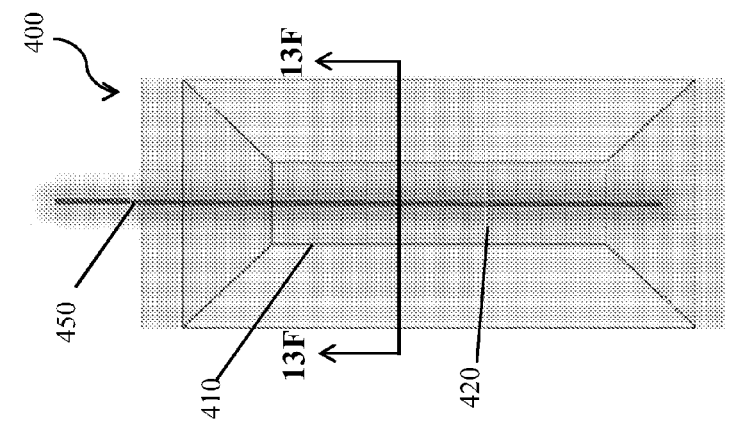
FIG. 13E is a schematic illustration of another therapeutic illumination assembly including one or more light emitting devices and a fiber housing vessel, according to one or more embodiments shown and described herein.
Figure 13F:
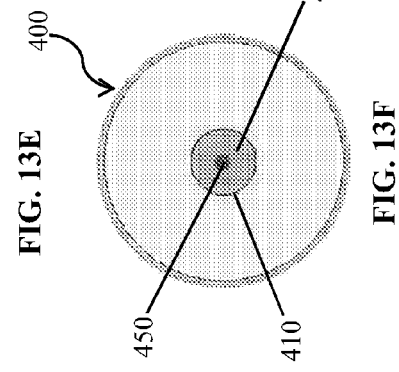
FIG. 13F is a cross-sectional illustration of the therapeutic illumination assembly of FIG. 13E, according to one or more embodiments shown and described herein.
Figure 13C:
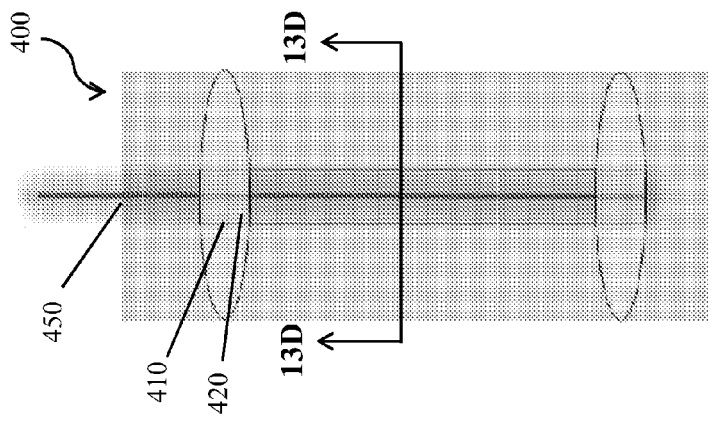
FIG. 13C is a schematic illustration of a therapeutic illumination assembly including one or more light emitting devices and a fiber housing vessel, according to one or more embodiments shown and described herein.
Figure 13D:
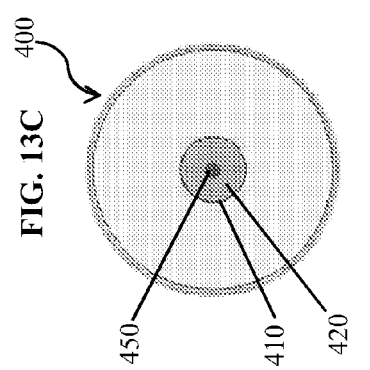
FIG. 13D is a cross-sectional illustration of the therapeutic illumination assembly of FIG. 13C, according to one or more embodiments shown and described herein.
Figure 13A:
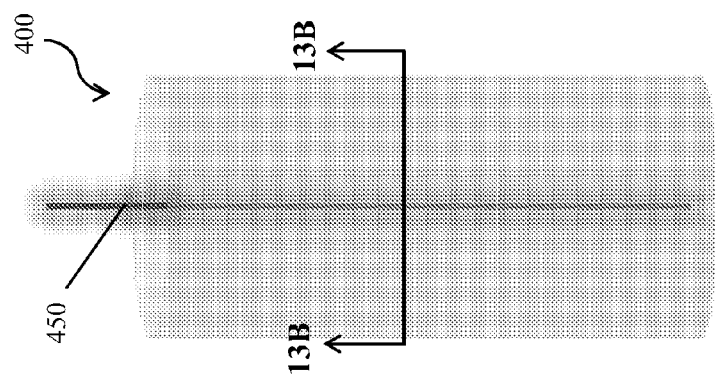
FIG. 13A is a schematic illustration of a therapeutic illumination assembly including one or more light emitting devices, according to one or more embodiments shown and described herein.
Figure 13B:
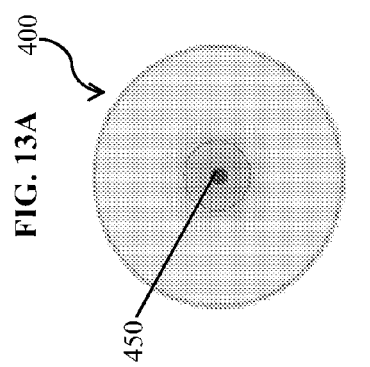
FIG. 13B is a cross-sectional illustration of the therapeutic illumination assembly of FIG. 13A, according to one or more embodiments shown and described herein.

Referring now to FIGS. 13A and 13B, the one or more luminal regions of the patient may comprise a variety of sizes and shapes and may comprise different tissue properties and capacities (e.g., biological fluid volume capacities). Luminal region composition and placement may be considered when designing the components of the therapeutic illumination assembly 400. In operation, the luminal regions of the patient may confine the biological fluid to a passage narrow enough such that the one or more light emitting devices 450 may be positioned within the luminal regions and may irradiate the biological fluid as it traverses the light emitting devices 450 without use of the fiber housing vessel 410.

Referring now to FIGS. 13C-13F, the fiber housing vessel 410 may be positioned within the luminal region of the patient to confine the biological fluid into a smaller channel, such that the light diffusing optical fiber or other emitting device 450 may effectively irradiate the biological fluid. FIGS. 13C-13D depict the fiber housing vessel 410 comprising a dual balloon system which confines the flowpath of biological fluid into a tube. FIGS. 13E-13F depict the fiber housing vessel 410 comprising a single balloon system in which the balloon blocks a portion (e.g., a majority) of the luminal region to confine the flow of biological fluid. Further, the fiber housing vessel 410 depicted in FIGS. 13C-13F may not need to be cross-sectionally centered within the luminal region. In operation, confining the biological fluid may ensure that enough light irradiates to the blood before the light is absorbed or scattered. Further, the fiber housing vessel 410 may comprise a stent, graft, or other expandable device to selectively and mechanically constrict the flow of biological fluid. Moreover, the fiber housing vessel 410 may be inserted into the patient and operated external to the patient, for example, an actuator located external to the patient may control the expansion of the fiber housing vessel 410, such that the fiber housing vessel 410 may fit tightly within the luminal region of the patient.

Referring now to FIGS. 14A-14F, 15A, and 15B, the fiber housing vessel 410 may comprise multiple housing vessel fluid pathways 420 that provide discrete housing locations for multiple light diffusing optical fibers or other light emitting devices 450 and that each provide a fluid channel to facilitate biological fluid flow. As depicted in FIGS. 14A and 14B, by spacing multiple light emitting devices 450 within a luminal region, the light emitting devices 450 may irradiate some or all the luminal region of the patient. As depicted in FIGS. 14C and 14D, the fiber housing vessel 410 may comprises a plurality of transparent tubes which may be held in a cross sectionally spaced arrangement by a mounting device, which may be positioned external or internal the luminal region of the patient and may be external to the patient. As depicted in FIGS. 14E and 14F, the fiber housing vessel 410 may comprise a plurality of balloons to provide multiple channels. For example, a dual balloon system may be used to place a number of tubes within the luminal regions of the patient such that biological fluid may flow by the light emitting devices 450 which may irradiate the biological fluid.

Figure 15B:
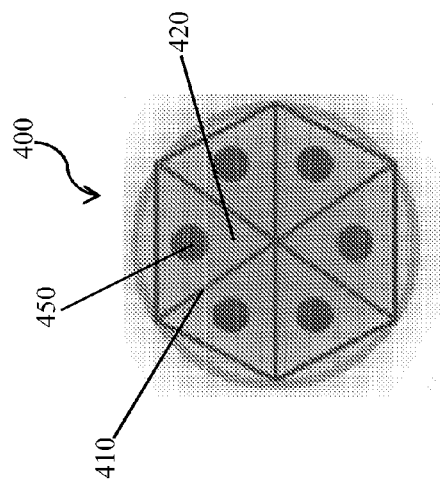
FIG. 15B is a schematic illustration of another therapeutic illumination assembly including one or more light emitting devices and a fiber housing vessel, according to one or more embodiments shown and described herein.
Figure 15A:
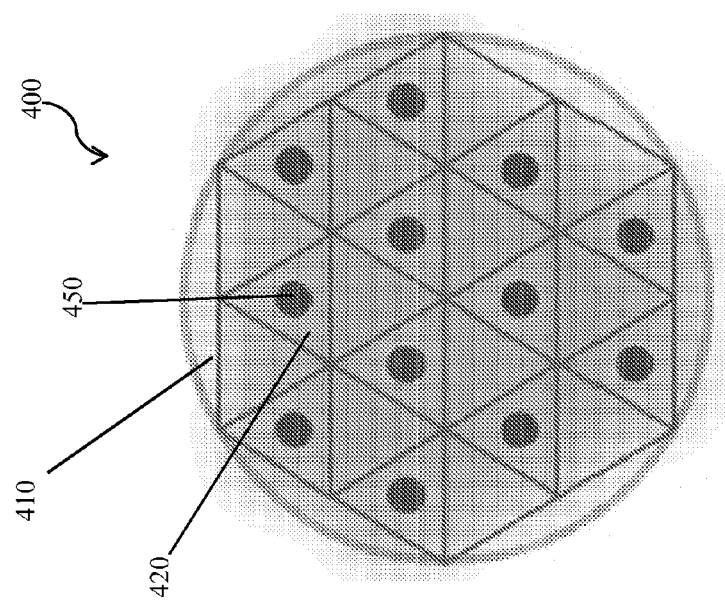
FIG. 15A is a schematic illustration of another therapeutic illumination assembly including one or more light emitting devices and a fiber housing vessel, according to one or more embodiments shown and described herein.

As depicted in FIGS. 15A and 15B, the fiber housing vessel 410 may comprise multiple housing vessel fluid pathways 420 that allow blood to freely flow through luminal regions of the patient. The fiber housing vessel 410 may comprise variety of sizes to account for the different sized luminal regions of the patient. Further, the fiber housing vessel 410 may comprise a stent (e.g., a transparent stent), a wire, a graft, a balloon, or other medical device comprising a polymer, ceramic, glass, metal, or other material and may be configured such that the fiber housing vessel 410 may separate one or more light emitting devices 450 equally or unequally within the housing vessel fluid pathways 420. Further, the fiber housing vessel 410 may be inserted into the patient and operated external to the patient, for example, an actuator located external to the patient may control the expansion of the fiber housing vessel 410, such that the fiber housing vessel 410 may fit tightly within the luminal region of the patient.

It is noted that recitations herein of a component of the present disclosure being "configured" in a particular way, to embody a particular property, or to function in a particular manner, are structural recitations, as opposed to recitations of intended use. More specifically, the references herein to the manner in which a component is "configured" denotes an existing physical condition of the component and, as such, is to be taken as a definite recitation of the structural characteristics of the component.

For the purposes of describing and defining the present invention it is noted that the term "about" is utilized herein to represent the inherent degree of uncertainty that may be attributed to any quantitative comparison, value, measurement, or other representation. The term "about" is also utilized herein to represent the degree by which a quantitative representation may vary from a stated reference without resulting in a change in the basic function of the subject matter at issue.

Having described the subject matter of the present disclosure in detail and by reference to specific embodiments thereof, it is noted that the various details disclosed herein should not be taken to imply that these details relate to elements that are essential components of the various embodiments described herein, even in cases where a particular element is illustrated in each of the drawings that accompany the present description. Further, it will be apparent that modifications and variations are possible without departing from the scope of the present disclosure, including, but not limited to, embodiments defined in the appended claims. More specifically, although some aspects of the present disclosure are identified herein as preferred or particularly advantageous, it is contemplated that the present disclosure is not necessarily limited to these aspects.

It is noted that one or more of the following claims utilize the term "wherein" as a transitional phrase. For the purposes of defining the present invention, it is noted that this term is introduced in the claims as an open-ended transitional phrase that is used to introduce a recitation of a series of characteristics of the structure and should be interpreted in like manner as the more commonly used open-ended preamble term "comprising."

The invention claimed is:

1. A therapeutic illumination assembly, comprising:
   a catheter comprising a catheter wall encircling a luminal fluid pathway, the catheter wall having an internal length configured for insertion into a patient at an insertion region and an external length fluidly coupled to internal length at the insertion region; and,
   a therapeutic illumination patch comprising a wound facing surface, one or more outer facing surfaces, and a plurality of light emitting point sources positioned on at least two outer facing surfaces of the plurality of outer facing surfaces to irradiate the insertion region and the therapeutic illumination patch when the plurality of light emitting point sources output light, the therapeutic illumination patch operable to have the internal length of the catheter pass through the wound facing surface and the outer facing surface at the insertion region,
   wherein the therapeutic illumination patch comprises a waveguide structurally and compositionally configured such that at least a portion of light emitted from the plurality of light emitting point sources into the waveguide is subject to internal reflection within the waveguide and refraction at the wound facing surface when being emitted from the waveguide.

2. The therapeutic illumination assembly of claim 1, wherein at least one light emitting point source of the plurality of light emitting point sources is positioned on an outer facing surface of the catheter wall proximal to the insertion region.

3. The therapeutic illumination assembly of claim 2, wherein light emitting point sources of the plurality of light emitting point sources encircle the catheter wall at the insertion region.

4. The therapeutic illumination assembly of claim 1, wherein the plurality of light emitting point sources are spaced apart from an outer facing surface of the catheter wall.

5. The therapeutic illumination assembly of claim 1, wherein the therapeutic illumination patch comprises an optically diffusive material.

6. The therapeutic illumination assembly of claim 1, wherein the wound facing surface is configured to be positioned adjacent to the patient over the insertion region.

7. The therapeutic illumination assembly of claim 1, wherein the plurality of light emitting point sources comprise a plurality of diodes.

8. The therapeutic illumination assembly of claim 7, wherein the plurality of diodes comprise one or more laser diodes, one or more light emitting diodes (LED), or a combination thereof.

9. The therapeutic illumination assembly of claim 1, further comprising a point source treatment fiber positioned within the luminal fluid pathway of the catheter, the point source treatment fiber comprises a further plurality of light emitting point sources intermittently positioned along a treatment length of the point source treatment fiber such that the further plurality of light emitting point sources irradiate the catheter when the further plurality of light emitting point sources emit light.

10. The therapeutic illumination assembly of claim 9, wherein the point source treatment fiber comprises a therapeutic optical fiber optically coupled to a therapeutic light source.

11. The therapeutic illumination assembly of claim 10, wherein the therapeutic optical fiber comprises a light diffusing optical fiber intermittently coated with an opaque coating such that uncoated portions of the light diffusing optical fiber comprise light emitting point sources of the plurality of light emitting point sources.

12. The therapeutic illumination assembly of claim 9, wherein the further plurality of light emitting point sources are equally spaced along the treatment length of the point source treatment fiber.

13. A method, comprising:
   inserting an internal length of a catheter into a patient through a wound facing surface and an outer facing surface of a plurality of outer facing surfaces of a therapeutic illumination patch, wherein the catheter comprises a catheter wall encircling a luminal fluid pathway, the catheter wall having an external length fluidly coupled to the internal length at an insertion region of the catheter, wherein the wound facing surface is configured to be positioned on the patient over the insertion region; and, irradiating the insertion region of the catheter using a plurality of light emitting point sources connected to at least two of the plurality of outer facing surfaces, wherein the therapeutic illumination patch comprises a waveguide structurally and compositionally configured such that at least a portion of light emitted from the plurality of light emitting point sources into the waveguide is subject to internal reflection within the waveguide and refraction at the wound facing surface when being emitted from the waveguide.

14. The method of claim 13, wherein the plurality of light emitting point sources are spaced apart from an outer facing surface of the catheter wall and wherein the step of irradiating the insertion region comprises emitting light from the plurality of light emitting point sources toward the insertion region.

15. The method of claim 13, wherein light emitting point sources of the plurality of light emitting point sources are positioned on an outer facing surface of the catheter wall proximal to the insertion region and wherein the method further comprises irradiating a percutaneous lesion proximal to the catheter.

16. The method of claim 13, further comprising inserting a point source treatment fiber comprising a further plurality of light emitting point sources intermittently positioned along a treatment length of the point source treatment fiber into the luminal fluid pathway of the catheter;

wherein the method further comprises irradiating the catheter using the further plurality of light emitting point sources.

17. A therapeutic illumination assembly, comprising:
a therapeutic illumination patch, including:
 a wound facing surface facing a first direction;
 a plurality of outer surfaces, including at least:
  a first outer surface facing a second direction, opposite the first direction; and,
  a second outer surface connecting the first outer surface and the wound facing surface; and,
 a through-hole;
a catheter engaged with the through-hole, the catheter including:
 a catheter wall encircling a liminal fluid pathway;
 an internal length protruding from the wound facing surface; and,
 an external length protruding from the first outer surface; and,
a plurality of light sources arranged on at least two outer surfaces of the plurality of outer surfaces;
wherein:
 the therapeutic illumination patch comprises a waveguide;
 the plurality of light sources are arranged to transmit light into the waveguide; and,
 the light is subject to internal reflection within the waveguide and refraction at the wound facing surface when being emitted from the waveguide.

18. The therapeutic illumination assembly of claim 17, wherein a first light source of the plurality of light sources is arranged on the second outer surface.

19. The therapeutic illumination assembly of claim 18, wherein:
 the therapeutic illumination patch further comprises a third outer surface connecting the first outer surface and the wound facing surface; and,
 a second light source of the plurality of light sources is connected to the third outer surface.

* * * * *

UNITED STATES PATENT AND TRADEMARK OFFICE
CERTIFICATE OF CORRECTION

| | |
|---|---|
| PATENT NO. | : 11,786,751 B2 |
| APPLICATION NO. | : 16/720841 |
| DATED | : October 17, 2023 |
| INVENTOR(S) | : Michael Lucien Genier et al. |

Page 1 of 1

It is certified that error appears in the above-identified patent and that said Letters Patent is hereby corrected as shown below:

In the Claims

In Column 11, Line 63, in Claim 1, delete "plurality of" and insert -- one or more --.

Signed and Sealed this
Twenty-third Day of July, 2024

Katherine Kelly Vidal
*Director of the United States Patent and Trademark Office*